United States Patent [19]

Randolph et al.

[11] Patent Number: 5,891,819
[45] Date of Patent: Apr. 6, 1999

[54] CATALYST COMPRISING HYDROGEN HALIDE, SULFONE, AND A PROMOTER

[75] Inventors: Bruce B. Randolph, Bartlesville, Okla.; Ronald G. Abbott, Kingwood, Tex.

[73] Assignee: Phillips Petroleum Company, Bartlesville, Okla.

[21] Appl. No.: 970,044

[22] Filed: Nov. 13, 1997

Related U.S. Application Data

[60] Division of Ser. No. 452,738, May 30, 1995, Pat. No. 5,723,715, which is a continuation-in-part of Ser. No. 950,334, Sep. 24, 1992, abandoned.

[51] Int. Cl.$^6$ ..................................................... B01J 27/02
[52] U.S. Cl. ......................... 502/216; 502/150; 502/168; 502/170; 502/224
[58] Field of Search ..................... 502/150, 168, 502/170, 216, 224

[56] References Cited

U.S. PATENT DOCUMENTS

| | | | |
|---|---|---|---|
| 3,678,120 | 7/1972 | Bloch | 260/668 |
| 3,708,553 | 1/1973 | Olah | 260/683.47 |
| 3,778,489 | 12/1973 | Parker et al. | 260/683.43 |
| 3,795,712 | 3/1974 | Torck et al. | 260/671 C |
| 3,887,635 | 6/1975 | Parker et al. | 260/683.47 |
| 3,928,487 | 12/1975 | McCaulay | 260/683.51 |
| 4,024,203 | 5/1977 | Torck et al. | 260/683.15 A |
| 4,058,575 | 11/1977 | Cahn et al. | 260/666 P |
| 4,069,268 | 1/1978 | Sisken et al. | 260/666 P |
| 4,094,924 | 6/1978 | Siskin et al. | 260/683.51 |
| 4,118,433 | 10/1978 | Innes | 260/683.51 |
| 4,120,912 | 10/1978 | Hulme | 260/683.47 |

FOREIGN PATENT DOCUMENTS 537589 of 0000 United Kingdom .

*Primary Examiner*—Glenn Caldarola
*Assistant Examiner*—In Suk Bullock
*Attorney, Agent, or Firm*—Charles W. Stewart

[57] ABSTRACT

A novel alkylation catalyst is described which is used in processes for alkylating olefin hydrocarbons with isoparaffin hydrocarbons to produce high octane alkylate products suitable for use as a blending component of gasoline motor fuel. The novel catalyst comprises a mixture of a hydrogen helide, a sulfone and a promoter. The novel alkylation catalyst is utilized in a novel process for alkylating olefin hydrocarbons with isoparaffin hydrocarbons.

16 Claims, No Drawings

CATALYST COMPRISING HYDROGEN HALIDE, SULFONE, AND A PROMOTER

This application is a divisional of application Ser. No. 08/452,738, filed May 30, 1995, now U.S. Pat. No. 5,723,715 which is a continuation-in-part of application Ser. No. 07/950,334, filed Sep. 24, 1992, now abandoned.

The present invention relates to a hydrocarbon conversion process and a catalyst composition to be utilized in said hydrocarbon conversion process. More particularly, the invention relates to an improved alkylation process for the production of an alkylate product by contacting hydrocarbon with a novel catalyst composition.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling said mixture to separate the catalyst from the hydrocarbons, and further separating the hydrocarbons, for example, by fractionation, to recover the alkylation reaction product. Normally, the alkylation reaction product is referred to as "alkylate", and it preferably contains hydrocarbons having seven to nine carbon atoms. In order to have the highest quality gasoline blending stock, it is preferred that the hydrocarbons formed in the alkylation process be highly branched.

One of the more desirable alkylation catalysts is hydrofluoric acid, however, the use of hydrofluoric acid as an alkylation catalyst has certain drawbacks. One of the primary problems with the use of hydrofluoric acid as an alkylation catalyst is that it is a highly corrosive substance and it is toxic to human beings. The toxicity of hydrofluoric acid to human beings is further complicated by the fact that anhydrous hydrofluoric acid is typically a gas at normal atmospheric conditions of one atmosphere of pressure and 70° F. It is possible for the vapor pressure of hydrofluoric acid at standard atmospheric conditions to create certain safety concerns when it is exposed to the atmosphere. These safety concerns are created by the ease with which hydrofluoric acid is vaporized and released into the atmosphere.

In spite of the potential problems with human toxicity and the corrosive characteristics of hydrofluoric acid, industry has in the past determined that the benefits from the use of hydrofluoric acid as an alkylation catalyst outweigh the potential problems. For instance, hydrofluoric acid is an extremely effective alkylation catalyst in that it permits the reaction of olefins by isoparaffins at low process pressures and low process temperatures. HF is particularly suited for use as a catalyst in the alkylation of butylenes and, in the case of the alkylation of propylene and anylenes, HF has been used as an effective catalyst whereas other alkylation catalysts, such as sulfuric acid, have been found to be not as effective in such alkylation services. Additionally, the alkylate formed from a hydrofluoric acid alkylation process is of a very high quality having such desirable properties as being a mixture of highly branched hydrocarbon compounds that provide a high octane motor fuel. Generally, it has been found that the alkylate produced by a hydrofluoric acid alkylation process has a higher octane value than that produced by typical sulfuric acid alkylation processes. Thus, it would be desirable to use an alkylation catalyst that has the desirable features of hydrofluoric acid catalyst but without having its high vapor pressure.

It is, therefore, an object of this invention to provide a novel alkylation catalyst having the desirable property of yielding a high quality alkylate when utilized in the alkylation of olefins with paraffins but having a lower vapor pressure than that of hydrofluoric acid.

A further object of this invention is to provide a process for the alkylation of olefins with paraffins in the presence of an alkylation catalyst having the desirable property of having a reduced vapor pressure but which produces a high quality alkylate product.

Thus, the process of the present invention relates to the alkylation of a hydrocarbon mixture comprising olefins and paraffins with a catalyst composition having an absence of a Lewis acid and comprising the components of a hydrogen halide, a sulfone, and a promoter selected from a group consisting of sulfuric acid, fluorosulfonic acid, and the sulfonic acids of the formula $RSO_3H$ wherein R is an alkyl group, an aromatic group, a halogenated alkyl group or a halogenated aromatic group.

The composition of the present invention has an absence of a Lewis acid and comprises the components of a hydrogen halide, a sulfone, and a promoter selected from a group consisting of sulfuric acid, fluorosulfonic acid, and the sulfonic acids of the formula $RSO_3H$ wherein R is an alkyl group, an aromatic group, a halogenated alkyl group or a halogenated aromatic group.

Other objects and advantages of the invention will be apparent from the detailed description of the invention and the appended claims.

The novel composition of the present invention is suitable for use as an alkylation catalyst and can comprise, consist of, or consist essentially of a hydrogen halide component, a sulfone component and a promoter selected from the group consisting of sulfuric acid, fluorosulfonic acid, and the sulfonic acids of the formula $RSO_3H$ wherein R is an alkyl group, an aromatic group, a halogenated alkyl group or a halogenated aromatic group. The novel composition can further have an absence of a Lewis acid.

The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form, but, generally, the hydrogen fluoride component utilized can have a small amount of water. The amount of water present in the catalyst composition in no event can be more than about 30 weight percent of the total weight of the hydrogen halide component, which includes the water, and preferably, the amount of water present in the hydrogen halide component is less than about 10 weight percent. Most preferably, the amount of water present in the hydrogen halide component is less than 5 weight percent. When referring herein to the hydrogen halide component, or more specifically, to a preferred hydrogen fluoride component, of the catalyst composition of the invention, it should be understood that these terms mean either the hydrogen halide component as an anhydrous mixture or a mixture that includes water. The references herein to weight percent water contained in the hydrogen halide component means the ratio of the weight of water to the sum weight of the water and hydrogen halide multiplied by a factor of 100 to place the weight ratio in terms of percent.

The sulfones suitable for use in this invention are the sulfones of the general formula $R-SO_2-R'$ wherein R and R' are monovalent hydrocarbon alkyl or aryl substituents, each containing from 1 to 8 carbon atoms.

Examples of such substituents include dimethylsulfone, di n-propylsulfone, diphenylsulfone, ethylmethylsulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

The sulfone component is an important component of the catalyst composition because of the several functions it serves and because of the physical properties that it imparts to the catalyst composition. One important function of the presence of the sulfone component in the composition is its vapor pressure depressant effect upon the overall catalyst composition. It is an essential aspect of this invention for the sulfone component to be soluble in the hydrogen halide component and for the sulfone component to be essentially immiscible with olefin and paraffin hydrocarbons so as to permit easy separation of the hydrocarbons from the catalyst composition. Also, it is essential for the presence of the sulfone component to have a minimal impact upon an alkylation reaction selectivity and activity.

To enhance the performance of a catalyst mixture including a hydrogen halide and a sulfone in the alkylation of olefins by isoparaffins, it has been discovered that a concentration of a promoter compound in the catalyst mixture can improve the selectivity of the catalyzed alkylation reaction toward the production of alkylate compounds having eight carbon atoms ($C_8$ compounds). This improvement in $C_8$ selectivity generally results in a concurrent reduction in the production of alkylate compounds having nine or more carbon atoms ($C_9+$ compounds). In addition to the improvements in $C_8$ selectivity and yield and the reduction of the undesirable $C_9+$ yield, improved is the selectivity toward the production of the more desirable $C_8$ compound of trimethylpentane (TMP) over that of dimetbylhexane (DMH). Thus, the ratio of TMP/DMH in an alkylate end product of any alkylation process is enhanced by the addition of a promoter to an alkylation catalyst comprising a hydrogen halide and a sulfone.

The promoter to be added to the catalyst mixture of hydrogen halide and sulfone can be any compound which suitably improves the catalyst performance so as to improve the selectivity of a catalyzed alkylation reaction toward the production of $C_8$ compounds of which the preferred compound is trimethylpentane. Generally, the compounds found to be effective in improving the selectivity of the olefin and isoparaffin alkylation reaction toward the production of $C_8$ compounds when added to the hydrogen halide and sulfone mixture are those selected from the group of promoters consisting of sulfuric acid, fluorosulfonic acid, and the sulfonic acids of the formula $RSO_3H$ wherein R can be an alkyl group, an aromatic group, a halogenated alkyl group, a halogenated aromatic group, or a halogen. The preferred promoter compounds are those selected from the group consisting of methanesulfonic acid, fluorosulfonic acid, and trifluoromethanesulfonic acid. The most preferred promoter compound is trifluoromethanesulfonic acid.

Having an absence of a Lewis acid from the catalyst mixture described herein is an important aspect of the invention for a variety of reasons. For instance, it is undesirable to have a corrosion promoting concentration of a Lewis acid in the catalyst mixture. It has been determined that many Lewis acids cannot effectively be used within a carbon steel process system because of their corrosive nature. Since an important aspect of the instant invention is the ability to use an alkylation catalyst mixture within a carbon steel reaction and process system, the presence of Lewis acids in the alkylation catalyst mixture at corrosive concentrations are not desired.

Another concern with the presence of a Lewis acid in the catalyst mixture is their general sensitivity to the presence of water. Many of the Lewis acids when exposed to water will react and decompose. This water sensitivity is particularly undesirable with the present catalyst mixture because of the hygroscopic nature of certain sulfones and hydrogen halides. Also, the inventive process conditions can be such that there can be present a concentration of water in the catalyst mixture.

Another problem associated with the presence of a Lewis acid in the catalyst mixture is the difficulty associated with the recovery of the Lewis acid from the catalyst mixture. In order to avoid separation problems, it is important for the catalyst mixture to be free of or to have an absence of a Lewis acid.

The term "Lewis acid" as used herein and in the claims refers to compounds having the formula $$R_nMX_{x-n}$$

wherein R is an alkyl, cycloalkyl, alkoxy or aryl group, these groups being optionally halogenated; X is a halogen or any other electronegative group such as, for example, $SO_3F$; M is a metal atom; x is a positive, non-zero integer and n has a value from 0 to x.

Generally, those skilled in the art of hydrogen fluoride catalyzed olefin alkylation processing have known that to obtain the highest quality of alkylate from the aforementioned olefin alkylation process, it is essential for the hydrogen fluoride catalyst to be as free from contaminating compounds as is feasible. It is generally known that small amounts of other compounds contained in the hydrogen fluoride catalyst of an olefin alkylation process can have detrimental effects upon product alkylate quality by negatively affecting the selectivity of the alkylation reaction toward the production of more desirable end-product, such as, for example, trimethylpentanes (TMP) in the case of the alkylation of butylenes by isobutane. It is further known to those skilled in the art that small amounts of components contained in a hydrogen fluoride alkylation catalyst can have a negative impact upon its activity toward the alkylation of olefins. Based upon the known effects of hydrogen fluoride catalyst contaminants upon the activity and selectivity of the alkylation process toward the production of high quality alkylate, one skilled in the art would expect that the addition of small to large amounts of a sulfone compound and other compounds to a hydrogen halide catalyst would have an enormously detrimental effect upon its catalytic performance.

However, it has been discovered that the presence of small quantities of certain, selective compounds along with quantities of a sulfone compound, in combination with a hydrogen halide catalyst, will have little negative impact on the catalytic performance of the resultant mixture in the alkylation of olefins by isoparaffins. Furthermore, it is further unexpected that, instead of having a detrimental impact upon the catalytic performance of the hydrogen halide and sulfone catalyst mixture, a small concentration, generally in an amount less than about 10 weight percent based upon the total weight of the hydrogen halide and sulfone, of a selectively chosen promoter component, in combination with the hydrogen halide and sulfone can, as earlier described, enhance the performance of the resultant composition as an alkylation process catalyst. The preferred concentration of the promoter in the alkylation catalyst comprising hydrogen halide and a sulfone compound can be in the range of from about 1 to about 10 weight percent of the hydrogen halide and sulfone. Most preferably, the concentration of the promoter compound in the alkylation catalyst, which includes hydrogen halide and a sulfone, will be in the range of from 1 to 6 weight percent.

Therefore, to take advantage of the vapor pressure depressant effects of the sulfone compound, it is desirable to utilize in the catalyst mixture a hydrogen halide to sulfone weight ratio in the range of from about 39:1 to 1:1. The preferred catalyst mixture should contain a weight ratio of hydrogen halide to sulfone component in the range of from about 19:1 to about 1:1 and, more preferably, the weight ratio shall range from 9:1 to 3:1. Also, to take advantage of the promoter effects or catalytic enhancement capabilities of the herein described selective promoter compound, the promoter compound as earlier described herein should have a concentration in the hydrogen halide and sulfone mixture of less than about 10 weight percent of the mixture. Preferably, the concentration range of the promoter will be from about 1 to about 10 weight percent, and most preferably, the concentration can range from 1 to 6 weight percent.

This novel alkylation catalyst composition solves many of the problems that heretofore have been encountered in typical alkylation processes that use hydrofluoric acid as an alkylation catalyst. For instance, this novel catalyst composition has a significantly lower vapor pressure than that of the standard hydrofluoric acid alkylation catalyst. The advantage from using an alkylation catalyst having a much lower vapor pressure than that of hydrofluoric acid is that a lesser amount of the acid catalyst will vaporize and enter into the atmosphere in cases where the catalyst is exposed to the atmosphere. In particular, when making a comparison between the novel catalyst composition and hydrofluoric acid, one notices a significant difference in the vapor pressures of the two catalysts. Since hydrofluoric acid has a substantial vapor pressure at typical atmospheric or ambient conditions, it is often in a vapor state at such conditions, and this vapor pressure makes it a possibly less controllable compound in cases where it is exposed to the environment.

The novel catalyst composition as described herein, solves many of the problems associated with the use of hydrofluoric acid as a catalyst since it provides the benefit of having a lower vapor pressure at ambient conditions than that of hydrofluoric acid. But, in addition to the benefit of having a lower vapor pressure at ambient conditions, the novel catalyst composition further can be utilized in typical alkylation processes to provide practical reaction rates at low operating pressures and low operating temperatures to produce a high quality alkylate product which is suitable for use as a blending component of gasoline motor fuel. A further benefit from the novel catalyst composition is that it is easier to handle commercially than hydrofluoric acid.

Alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel.

Preferably, isobutane is selected as the isoparaffin reactant and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

In order to improve selectivity of the alkylation reaction toward the production of the desirable highly branched aliphatic hydrocarbons having seven or more carbon atoms, in addition to using the promoter compounds described herein, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5:1 to about 20:1; and, most preferably, it shall range from 8:1 to 15:1. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentrations as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon, such nonreactive normal paraffin impurities tend to accumulate in the alkylation system. Consequently, process charge streams and/or recycle streams which contain substantial amounts of normal paraffin impurities are usually fractionated to remove such impurities and maintain their concentration at a low level, preferably less than about 5 volume percent, in the alkylation process.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the quality of alkylate product obtained. With this in mind, the present process, when operated as a batch operation, is characterized by the use of vigorous mechanical stirring or shaking of the reactants and catalyst.

In continuous operations, in one embodiment, reactants may be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. If desired, a portion of the catalyst can be continuously regenerated or reactivated by any suitable treatment and returned to the alkylation reactor.

The following examples demonstrate the advantages of the present invention. These examples are by way of illustration only, and are not intended as limitations upon the invention as set out in the appended claims.

EXAMPLE I

This Example I describes the method which utilizes batch reactions to test the feasibility of adding a promoter compound to a hydrogen fluoride and sulfolane mixture used as a catalyst for the alkylation of mono-olefins by isoparaffins. Data are presented to demonstrate the unexpectedly improved properties of the alkylate product from such a catalytic process and to demonstrate that for certain concentration ranges the catalyst mixture unexpectedly provides a good quality alkylate.

HF/sulfolane mixtures were evaluated for alkylation performance in batch reactions at 90° F. In a typical trial, the desired amount of sulfolane and promoter, if required, was added to a 300 mL monel autoclave under a blanket of nitrogen. Anhydrous HF was then introduced into the autoclave and heated to 90° F. with stirring at 500 RPM. The stirring was then increased to 2500 RPM, and an 8.5:1 isobutane:2-butenes mixture was added with nitrogen backpressure at a rate of 100 mL/min. at a pressure of 100–150 psig. After 5 minutes, the stirring was stopped, followed by the transfer of the reactor contents to a Jerguson gauge for phase separation. The hydrocarbon product was then characterized by gas chromatography.

The data presented in Table I were obtained by using the experimental method described in this Example I. The data demonstrate the improvement in the selectivity of the alkylation process toward the production of the highly desirable trimethylpentanes by utilizing a concentration of the indicated promoter. Also, the data demonstrate that the ratio of trimethylpentanes to dimethylhexanes contained in the alkylation product as a function of the weight percent sulfolane in the catalyst mixture is improved by use of the promoter.

TABLE I

|  | Test Samples | | | | |
| --- | --- | --- | --- | --- | --- |
|  | No. 1 | No. 2 | No. 3 | No. 4 | No. 5 |
| Promoter | none | FSA* | TFA** | TFA | FSA |
| mL HF | 65 | 65 | 65 | 65 | 65 |
| mL sulfolane | 35 | 35 | 35 | 35 | 35 |
| mL promoter | 0 | 6 | 6 | 3 | 3 |
| mL Feed | 170 | 150 | 150 | 150 | 150 |
| % TMP | 32.8 | 43.3 | 55.4 | 60.00 | 47.2 |
| % DMH | 11.2 | 11.7 | 11.9 | 13.3 | 12.8 |
| TMP:DMH | 2.9 | 3.7 | 4.7 | 4.5 | 3.7 |
| C9+ | 39.3 | 26.1 | 13.4 | 9.6 | 25.0 |
| Conversion | 98.8 | 100 | 100 | 100 | 100 |
| Organic fluorides | 0.00 | 0.00 | 1.7 | 0.64 | 0.00 |

*FSA is Fluorosulfonic acid
**TFA is Trifluoromethanesulfonic acid

EXAMPLE II

This Example II describes the steady state evaluation method for testing the feasibility of adding a promoter compound to a hydrogen fluoride and sulfolane mixture used as a catalyst for the alkylation of mono-olefins by isoparaffins. Data are presented to demonstrate that for certain concentration ranges the catalyst mixture unexpectedly provides a good quality alkylate.

A reactor was constructed to enable steady state evaluation of HF/sulfolane alkylation catalysts using a 300 mL monel riser reactor. A 10:1 isobutane:2-butenes feed was introduced into the riser at a rate of 300 mL/hour through a solid liquid stream nozzle. The reactor effluent flowed into a monel Jerguson gauge for phase separation. The hydrocarbon phase was passed through alumina, collected and then analyzed by standard gas chromatography.

Presented in Table II are data obtained by using the experimental method described in this Example II. The data presented in Table II represent the alkylate analysis at the given elapsed time into the experimental process run for the represented catalyst composition. Noted is the enormous improvement in alkylate quality obtained from the experiment utilizing a catalyst having a promoter vis-a-vis one that does not use a promoter. Not only is there a significantly greater quantity of $C_8$ compounds in the alkylate product, but the selectivity toward producing TMP is greater and, compared to a catalyst having a similar HF to sulfolane ratio, the undesirable organic fluoride production is smaller. These data demonstrate the unexpected improvements in catalytic activity of an HF/sulfolane catalyst mixture resulting from the addition of a sulfonic acid promoter.

TABLE II

| | 98/2 HF/H$_2$O | 50/45/5 HF/ Sulfolane/ TFA | 60/40 HF/ sulfolane | 50/50 HF/ sulfolane | 54/36/10 HF/ Sulfolane/ FSA |
|---|---|---|---|---|---|
| Time, hrs. | 9 | 6 | 9 | 9 | 24 |
| C8 | 75.9 | 84.6 | 44.1 | 29.4 | 59.6 |
| TMP | 64.2 | 70.2 | 35.2 | 22.1 | 48.7 |
| DMH | 11.7 | 14.2 | 8.83 | 7.16 | 10.7 |
| TMP/DMH | 5.50 | 4.94 | 3.98 | 3.09 | 4.54 |
| C9+ | 11.6 | 5.82 | 19.9 | 43.2 | 15.9 |
| R + M/2 | 93.3 | 93.3 | 90.7 | 86.8 | 91.9 |
| Fluorides | 0.08 | 0.32 | 4.50 | 14.2 | 0.0 |
| % conversion | 100.0 | 100.0 | 100.0 | 83.3 | 100.0 |

While this invention has been described in terms of the presently preferred embodiment, reasonable variations and modifications are possible by those skilled in the art. Such variations and modifications are within the scope of the described invention and the appended claims.

that which is claimed is:

1. A composition having an absence of a Lewis acid and comprising the components of:
   a hydrogen halide and a sulfone wherein the weight ratio of said hydrogen halide component to said sulfone component in said composition is in the range of from about 39:1 to about 1:1; and
   a promoter selected from a group consisting of sulfuric acid, fluorosulfonic acid, and a sulfonic acid of the formula R-SO$_3$H wherein R is an alkyl group, an aromatic group, a halogenated alkyl group, or a halogenated aromatic group.

2. A composition as recited in claim 1, wherein said hydrogen halide component is hydrogen fluoride.

3. A composition as recited in claim 2, wherein said promoter is present at a concentration of less than about 10 weight percent of the halogen halide and sulfone components.

4. A composition as recited in claim 1, wherein said sulfone component is sulfolane.

5. A composition as recited in claim 4, wherein the weight ratio of said hydrogen halide component to said sulfone component in said composition is in the range of from about 39:1 to about 1:1.

6. A composition as recited in claim 5, wherein said promoter is present at a concentration of less than about 10 weight percent of the hydrogen halide and sulfone components.

7. A composition as recited in claim 4, wherein said hydrogen halide component is hydrogen fluoride.

8. A composition as recited in claim 7, wherein the weight ratio of said hydrogen halide component to said sulfone component in said composition is in the range of from about 39:1 to about 1:1.

9. A composition as recited in claim 8, wherein said promoter is present at a concentration of less than about 10 weight percent of the hydrogen halide and sulfone components.

10. A composition suitable for use as a catalyst for the alkylation of olefins by paraffins, said composition having an absence of a Lewis acid and comprising:
    hydrogen fluoride and sulfolane present in said composition at a weight ratio of hydrogen fluoride to sulfolane in the range of from about 39:1 to about 1:1, and
    a promoter selected from a group consisting of sulfuric acid, fluorosulfonic acid, and a sulfonic acid of the formula RSO$_3$H, wherein R is an alkyl group, an aromatic group, a halogenated alkyl group, or a halogenated aromatic group, and wherein said promoter is present in said composition at a concentration of less than about 10 weight percent of the hydrogen fluoride and sulfolane.

11. A composition as recited in claim 10, wherein said promoter is selected from the group consisting of methanesulfonic acid, fluorosulfonic acid and trifluoromethanesulfonic acid.

12. A composition as recited in claim 11, wherein the weight ratio of hydrogen fluoride to sulfolane in said composition is in the range of from about 19:1 to about 1:1.

13. A composition as recited in claim 12, wherein said promoter is present in said composition at a concentration in the range of from about 1 to about 10 weight percent of the hydrogen fluoride and sulfolane.

14. A composition as recited in claim 13, wherein the weight ratio of said hydrogen fluoride component to said sulfolane component in said composition is in the range of from about 9:1 to about 3:1.

15. A composition as recited in claim 12, wherein said promoter is present in said composition at a concentration in the range of from about 1 to about 6 weight percent of the hydrogen fluoride and sulfolane.

16. A composition consisting of the components of:
    a hydrogen halide and a sulfone wherein the weight ratio of said hydrogen halide component to said sulfone component in said composition is in the range of from about 39:1 to about 1:1; and
    a promoter selected from the group consisting of sulfuric acid, fluorosulfonic acid, and a sulfonic acid of the formula R-SO$_3$H wherein R is an alkyl group, an aromatic group, a halogenated alkyl group, or a halogenated aromatic group.

* * * * *